US009492387B2

(12) United States Patent
Betageri et al.

(10) Patent No.: US 9,492,387 B2
(45) Date of Patent: Nov. 15, 2016

(54) TERNARY MIXTURE FORMULATIONS

(75) Inventors: Guru V. Betageri, Chino Hills, CA (US); Sunil A. Agnihotri, Exton, PA (US); Kumaresh Soppimath, Monmouth Junction, NJ (US)

(73) Assignee: WESTERN UNIVERSITY OF HEALTH SCIENCES, Pomona, CA (US)

( * ) Notice: Subject to any disclaimer, the term of this patent is extended or adjusted under 35 U.S.C. 154(b) by 0 days.

(21) Appl. No.: 13/881,381

(22) PCT Filed: Oct. 31, 2011

(86) PCT No.: PCT/US2011/058570
§ 371 (c)(1),
(2), (4) Date: Jul. 15, 2013

(87) PCT Pub. No.: WO2012/058668
PCT Pub. Date: May 3, 2012

(65) Prior Publication Data
US 2013/0310397 A1 Nov. 21, 2013

Related U.S. Application Data

(60) Provisional application No. 61/408,248, filed on Oct. 29, 2010.

(51) Int. Cl.
*A61K 9/14* (2006.01)
*A61K 31/235* (2006.01)
*A61K 9/16* (2006.01)
*A61K 47/24* (2006.01)
*A61K 9/107* (2006.01)
*A61K 47/40* (2006.01)
*A61K 31/496* (2006.01)
*A61K 31/216* (2006.01)

(52) U.S. Cl.
CPC .............. *A61K 9/14* (2013.01); *A61K 9/1075* (2013.01); *A61K 9/1617* (2013.01);
(Continued)

(58) Field of Classification Search
CPC ... Y10S 977/801; Y10S 977/89; A61K 9/10; A61K 9/1075; A61K 9/14; A61K 31/56; A61K 2300/00; A61K 8/97; A61K 9/5026; A61K 9/5138; A61K 9/5146; A61K 31/496; A61K 31/235; A61K 31/216; A61K 47/24; A61K 47/40; A61K 9/1617; A61K 9/1635; A61K 9/1652; A61K 9/1676; A61K 9/1694
See application file for complete search history.

(56) References Cited

U.S. PATENT DOCUMENTS 6,086,376 A * 7/2000 Moussa et al. ................ 434/45
6,337,092 B1   1/2002 Khan et al.
(Continued)

FOREIGN PATENT DOCUMENTS

WO    98/07414 A1    2/1998
WO    99/49846 A2    10/1999
(Continued)

OTHER PUBLICATIONS

PCT International Search Report and Written Opinion of PCT International Application No. PCT/US2011/058570 dated Sep. 6, 2012.
English translation of Office Action in corresponding JP Application No. 2013-536906, dated Jul. 7, 2015.

*Primary Examiner* — Aradhana Sasan
(74) *Attorney, Agent, or Firm* — J.A. Lindeman & Co., PLLC

(57) ABSTRACT

The invention relates to a novel free-flowing powder pharmaceutical formulation for the delivery of a poorly-water-soluble drug substance that increases the solubility and bioavailability of the poorly-water soluble drug substance, as well as to a method of making the free-flowing powder pharmaceutical formulation. The invention also relates to dispersed particles that disperse instantaneously from the free-flowing powder formulation when the formulation is added to water, aqueous solvent, or organic solvent, wherein the bulk distribution of the poorly-water soluble drug substance of the free-flowing powder formulation in the dispersed particles is uniform. Such dispersed particles increase the bioavailable surface area of the poorly water-soluble drug substance and facilitate the drug substance's dissolution.

6 Claims, 8 Drawing Sheets

(52) U.S. Cl.
CPC .......... *A61K 9/1635* (2013.01); *A61K 9/1652* (2013.01); *A61K 9/1676* (2013.01); *A61K 9/1694* (2013.01); *A61K 31/216* (2013.01); *A61K 31/235* (2013.01); *A61K 31/496* (2013.01); *A61K 47/24* (2013.01); *A61K 47/40* (2013.01)

(56) References Cited

U.S. PATENT DOCUMENTS

| | | | |
|---|---|---|---|
| 6,682,761 B2 * | 1/2004 | Pace | ........................ A61K 9/145 264/5 |
| 2002/0037316 A1 | 3/2002 | Weers et al. | |
| 2002/0150621 A1 | 10/2002 | Kohane et al. | |
| 2003/0129250 A1 | 7/2003 | Batycky et al. | |
| 2003/0180367 A1 | 9/2003 | Parikh et al. | |
| 2004/0062778 A1 | 4/2004 | Shefer et al. | |
| 2004/0115226 A1 | 6/2004 | Li et al. | |

FOREIGN PATENT DOCUMENTS

| | | | |
|---|---|---|---|
| WO | WO 02/00201 A2 * | 1/2002 | ............... A61K 9/20 |
| WO | 2006060325 A2 | 6/2006 | |
| WO | 2008066298 A1 | 6/2008 | |
| WO | 2012058668 A2 | 5/2012 | |

* cited by examiner

TERNARY MIXTURE FORMULATIONS

CROSS-REFERENCE TO RELATED APPLICATIONS

Priority is claimed to U.S. Application Ser. No. 61/408,248 filed 29 Oct. 2010, the entire disclosure of which is incorporated herein by reference.

FIELD OF THE INVENTION

The invention relates to a novel free-flowing powder pharmaceutical formulation for the delivery of a poorly-water-soluble drug substance that increases the solubility and bioavailability of the poorly-water soluble drug substance, as well as to a method of making the free-flowing powder pharmaceutical formulation. The invention also relates to dispersed particles that disperse instantaneously from the free-flowing powder formulation when the formulation is added to water, aqueous solvent, or organic solvent, wherein the bulk distribution of the poorly-water soluble drug substance of the free-flowing powder formulation in the dispersed particles is uniform. Such dispersed particles increase the bioavailable surface area of the poorly water-soluble drug substance and facilitate the drug substance's dissolution.

BACKGROUND

The therapeutic effectiveness of a drug depends on its bioavailability. More specifically, the term "bioavailibilty" refers to a measure of the rate and extent to which the active ingredient or active moiety is absorbed from a drug product and becomes available at the site of action. See Food and Drug Administration regulation C.F.R. 21 §320.1(a). In particular, the bioavailability of a drug once it is administered correlates to the drug's solubility. See U.S. Dept. of Health and Human Services, FDA, Center for Drug Evaluation and Research "Guidance for Industry: Waiver of In Vivo Bioavailability and Bioequivalence Studies for Immediate-Release Solid Oral Dosage Forms Based on a Biopharmaceutics Classification System," (August 2000). As of 2008, approximately 30% of the drugs that appeared on the World Health Organization (WHO) Essential Drug List were poorly water-soluble, based on the Food and Drug Administration (FDA)'s Biopharmaceutics Classification System (BCS) Tam J M, et al. J. Pharm. Sci. 97(11):4915-33 (2008). The poor dissolution of these drugs often results in the drugs having low and highly variable bioavailabilities. A major obstacle of successfully commercializing poorly water-soluble drugs is the difficulty of enhancing their dissolution rates and extents of dissolution. Therefore, a need exists to develop pharmaceutical formulations that increase the solubilities of poorly water-soluble drugs.

The preparation of a pharmaceutical formulation that comprises a poorly water-soluble drug generally requires a step that dissolves the poorly water-soluble drug in an organic solvent in combination with a lipid substance. In addition, such preparations frequently require that solubilizing aids be used to enhance the dissolution of poorly water-soluble drugs. However, solubilizing aids typically need to be dissolved in water or water-miscible solvents rather than organic solvents. Predictably, the step of mixing the organic solution that contains the drug and the lipid with the aqueous solution that contains the solubilizing aid creates the expectation that the solutes will precipitate out of solution. The consequence of a precipitation event is that a powder formulation prepared from the solution would no longer be homogenous, thereby complicating the performance or processing of the formulation. This invention, however, optimizes a composition of organic and aqueous solvents, surfactant, a poorly water-soluble drug substance, and a solubilizing aid to obtain a clear, non-precipitating, homogenous solution that can be easily converted into a free flowing powder formulation.

SUMMARY OF THE INVENTION

This invention is directed to a novel, commercially viable process for manufacturing a formulation for poorly water-soluble drugs that increases the solubility and bioavailability of these drugs. More specifically, the process of the invention ("the process") yields a free-flowing powder, wherein the process: 1) dissolves a lipid or a combination of lipids, a poorly water-soluble drug substance or combination of poorly water-soluble drug substances, and a surfactant or a combination of surfactants in a partially water-miscible or non-water-miscible solvent, or combination of such solvents, to form a first solution; 2) separately dissolves a solubilizing aid, or combination of solubilizing aids in water to form an aqueous solution and then adds a water-miscible solvent or combination of water-miscible solvents to the aqueous solution to form a second solution; 3) mixes the first and second solutions; and 4) either spray dries or coats onto a surface of a substrate the mixture of the solutions to form a free-flowing, non-sticky powder having a uniform dispersion of the poorly water-soluble drug, the phospholipid substance, and the surfactant ingredients.

The invention also relates to a free-flowing powder formulation containing a homogenous mixture of: a lipid or mixture of lipids; a poorly water-soluble drug substance or a combination of poorly water-soluble drug substances; a surfactant or a combination of surfactants; and a solubilizing aid, or a combination of solubilizing aids. In other words, one embodiment of the invention is a free-flowing powder formulation comprising a homogenous mixture of at least one lipid; at least one poorly water-soluble drug substance; at least one surfactant, and at least one solubilizing aid.

Upon contact with water, an aqueous solvent, or organic solvent, the free flowing powder instantaneously disperses into particles that contain the poorly water-soluble drug, the phospholipid substance, the surfactant, and the solubilizing aid ingredients. The dispersed particles, which may, in certain embodiments, be nanoparticles, increase the solubility of the poorly water-soluble drug, in part, by increasing the surface area exposure of the drug. The poorly water-soluble drug contained in the particles may also release into an aqueous fluid, where it will be available for in vivo absorption in bodily fluids, for example, when the formulation is ingested and disperses into particles in the aqueous fluids of the digestive tract. In turn, the particles facilitate the increased in vivo dissolution and absorption of the poorly water-soluble drug in comparison to the same poorly water-soluble drug administered in pure form.

DETAILED DESCRIPTION

Figure 1:
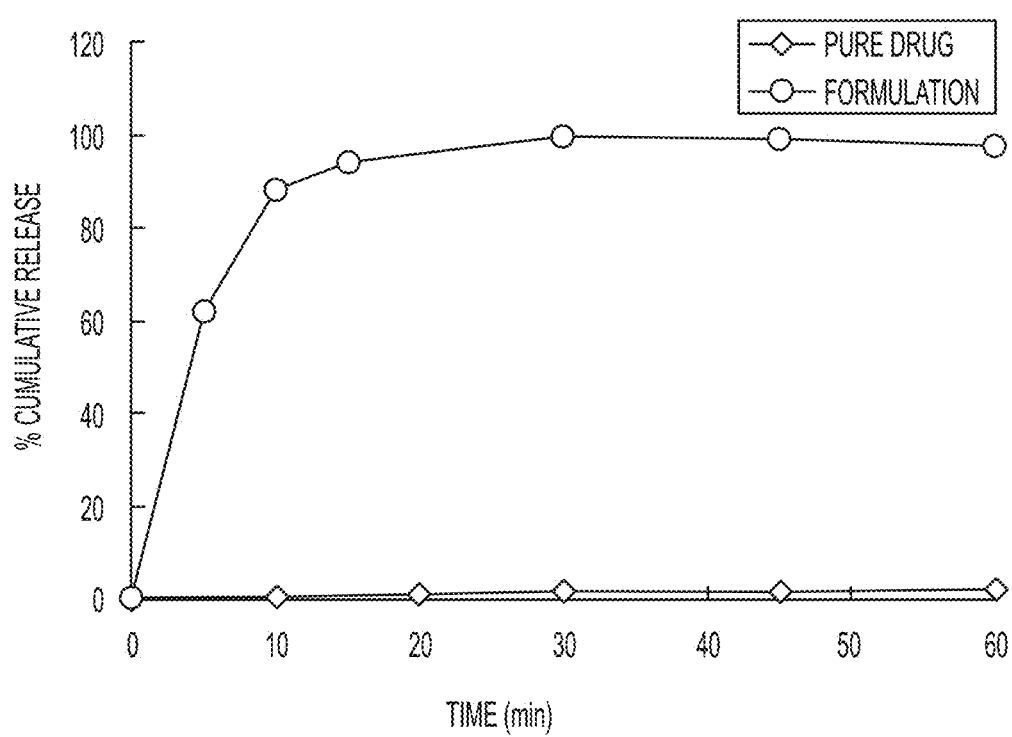
FIG. 1 shows the dissolution profile of itraconazole from a free-flowing powder itraconazole formulation comprising dimyristoyl-phosphoglycerol as compared to the dissolution profiles of an equivalent amount of pure itraconazole.

The invention relates to a novel pharmaceutical formulation that increases the solubility and bioavailability of poorly water-soluble drug substances, as compared to currently used formulations for such drugs. Disclosed herein is the composition and process for making the foregoing formulation. More, particularly, the process of the invention ("the process") dissolves a lipid, a poorly water-soluble drug substance, and a surfactant in a water partially-miscible or water non-miscible solvent to form a first solution; dissolves a solubilizing aid or combination of solubilizing aids in water to form a second solution; adds a water-miscible solvent or combination of water-miscible solvents to the second solution to form a third solution; combines the first solution and with the third solution to form a clear, homogenous solution; and produces a free flowing powder by removing the water partially-miscible or non-miscible solvent, water, and water-miscible solvents by methods known in the art, including spray drying, and coating the mixture onto a surface of an inert substrate (e.g., nonpareil beads). Accordingly, the process produces a free-flowing powder formulation comprising: a lipid or combination of lipids; a poorly water-soluble drug substance or combination of poorly water-soluble drug substances; a surfactant or combination of surfactants; a solubilizing aid, or combination of solubilizing aids. Each step of the process is described below.

Lipids

The lipid component of the free-flowing powder formulation of the invention may be any pharmaceutically acceptable lipid known in the art. In preparing the free-flowing powder formulation of the invention, lipid components including neutral lipids, positively-charged lipids, negatively-charged lipids, amphoteric lipids such as phospholipids, and cholesterol are advantageously used. As defined herein, the lipid component of the free-flowing powder formulation of the invention of the invention are intended to encompass a single species of lipid (such as a particular phospholipid) or combinations of such lipids, either of one type such as combinations of phospholipids (for example, phosphatidylcholine plus phosphatidyl ethanolamine) or of different types (such as a phospholipid plus a charged lipid or a neutral lipid). Combinations comprising a multiplicity of different lipid types are also advantageously encompassed by the proliposomal compositions of the invention (see, Lehninger, 1975, Biochemistry, 2d ed., Chapters 11 & 24, Worth Publishers: New York; and Small, 1986, "From alkanes to phospholipids," Handbook of Lipid Research: Physical Chemistry of Lipids, Volume 4, Chapters 4 and 12, Plenum Press: New York, which are incorporated in their entireties herein). It is also understood herein that the term "phospholipid" refers all natural as well as synthetic phospholipids, as well as combinations of phospholipids. More specifically, phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, known as a phospholipid bilayer or a lamella, converge into a sphere and in doing so entrap some of the aqueous medium, and whatever may be dissolved or suspended in it, in the core of the sphere, such as, the poorly-water soluble drug substance, solubilizing aid, or surfactant components, or combinations thereof, of the free-flowing powder formulation of the invention comprises.

Examples of suitable phospholipids that may be used in making the free-flowing powder formulations of the invention are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)] sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt, or combinations thereof. In addition, preferable phospholipids include, but are not limited to, soy phosphatidyl choline, egg phosphatidyl choline, dimyristoyl-phosphocholine, dimyristoyl-phosphoglycerol, distearoyl-phosphatidylcholine, distearoyl-phosphatidyl glycerol, and dipalmitoyl-phosphocholine.

The process also advantageously tolerates the use of phospholipids with either low or high phase transition temperatures. In some embodiments of the invention, however, the process may be more suitable for phospholipids with low transition phase temperatures. Thus, in certain embodiments, the formulation of the invention includes one or more phospholipids selected according to their transition temperature. For example, by administering a formulation which includes a phospholipid or combination of phospholipids which have a phase transition temperature higher than the patient's body temperature, the release of the active ingredient can be slowed down. On the other hand, rapid release can be obtained by including in the formulation phospholipids having low transition temperatures.

Poorly Water-Soluble Drug Substances

The poorly water-soluble drug substance component of the formulation of the invention are generally compounds having solubility not greater than about 10 mg/ml in water at 37° C. In various embodiments, the compound solubility is not greater than about 1 mg/ml. In other embodiments, compound solubility is not greater than about 0.1 mg/ml. A synonymous term to "poorly soluble" is "low aqueous solubility." Solubility in water for many drugs can be readily determined from standard pharmaceutical reference books, for example, The Merck Index, 13th ed., 2001 (published by Merck & Co., Inc., Rahway, N.J.); the United States Pharmacopoeia, 24th ed. (USP 24), 2000; The Extra Pharmacopoeia, 29th ed., 1989 (published by Pharmaceutical Press, London); and the Physicians Desk Reference (PDR), 2005 ed. (published by Medical Economics Co., Montvale, N.J.).

It is also understood herein, that poorly water-soluble drugs may include drugs that are classified by the U.S. Food and Drug Administration ("the FDA") as Biopharmaceutics Classification System (BCS) II and BCS IV drugs. The BCS classification system provides guidance for predicting intestinal drug absorption of drug molecules. BCS Class II drugs are characterized by having a profile of high permeability and low solubility, whereas BCS Class IV drugs are characterized by having a profile of low permeability and low solubility. Thus, in various embodiments of the process, the "poorly water-soluble active agents" component includes BCS Class II and Class IV drugs.

Certain embodiments of the process may also include one or more drugs that are selected from sparingly water-soluble drugs, slightly water-soluble drugs, very slightly water-soluble drugs, and water-insoluble drugs. More specifically, sparingly soluble drugs require 30 to 100 parts of water to one part of solute to achieve solubility. Slightly water-soluble drugs require 100 to 1,000 parts of water to one part of solute to achieve solubility. Very slightly water-soluble drugs require 1,000 to 10,000 parts of water to one part of solute to achieve solubility. Water-insoluble drugs require more than 10,000 parts of solvent to one part of solute to achieve solubility.

Solubility of drug substances may also be dependent on pH. For example, drug substances of the invention also include those which have low native solubility in the fluid of the environment of use. In various embodiments, the environment of use may be the gastrointestinal tract, which contains within specific regions fluids varying in pH. The pH of fasted stomach fluids is typically reported in the range of 1 to 2. The pH of small intestinal fluid is typically reported in the range of about 4.7 to 7.3. The pH of duodenal fluid has been reported in the range of about 4.7 to 6.5, those of the upper jejunum in the range of about 6.2 to 6.7, and lower jejunum, about 6.2 to 7.3. Drug substances of the invention can be those drugs that exhibit low native solubility in any one of the aforementioned environments of use, but which in another environment of use may have a high native solubility.

As discussed above, drug substances suitable for use in the invention can also be identified generally by drug class, e.g., Class II or Class IV, according to the BCS (Biopharmaceutical Classification System). Exemplary medicaments of the invention can also be identified by therapeutic class, which includes, but are not limited to, medicaments which are abortifacients, ACE inhibitors, α- and β-adrenergic agonists, α- and β-adrenergic blockers, adrenocortical suppressants, adrenocorticotropic hormones, alcohol deterrents, aldose reductase inhibitors, aldosterone antagonists, anabolics, analgesics (including narcotic and non-narcotic analgesics), androgens, angiotensin II receptor antagonists, anorexics, antacids, anthelminthics, antiacne agents, antiallergics, antialopecia agents, antiamebics, antiandrogens, antianginal agents, antiarrhythmics, antiarteriosclerotics, antiarthritic/antirheumatic agents, antiasthmatics, antibacterials, antibacterial adjuncts, anticholinergics, anticoagulants, anticonvulsants, antidepressants, antidiabetics, antidiarrheal agents, antidiuretics, antidotes to poison, antidyskinetics, antieczematics, antiemetics, antiestrogens, antifibrotics, antiflatulents, antifungals, antiglaucoma agents, antigonadotropins, antigout agents, antihistaminics, antihyperactives, antihyperlipoproteinemics, antihyperphosphatemics, antihypertensives, antihyperthyroid agents, antihypotensives, antihypothyroid agents, anti-inflammatories, antimalarials, antimanics, antimethemoglobinemics, antimigraine agents, antimuscarinics, antimycobacterials, antineoplastic agents and adjuncts, antineutropenics, antiosteoporotics, antipagetics, antiparkinsonian agents, antipheochromocytoma agents, antipneumocystis agents, antiprostatic hypertrophy agents, antiprotozoals, antipruritics, antipsoriatics, antipsychotics, antipyretics, antirickettsials, antiseborrheics, antiseptics/disinfectants, antispasmodics, antisyphylitics, antithrombocythemics, antithrombotics, antitussives, antiulceratives, antiurolithics, antivenins, antiviral agents, anxiolytics, aromatase inhibitors, astringents, benzodiazepine antagonists, bone resorption inhibitors, bradycardic agents, bradykinin antagonists, bronchodilators, calcium channel blockers, calcium regulators, carbonic anhydrase inhibitors, cardiotonics, CCK antagonists, chelating agents, cholelitholytic agents, choleretics, cholinergics, cholinesterase inhibitors, cholinesterase reactivators, CNS stimulants, contraceptives, COX-I and COX II inhibitors, debriding agents, decongestants, depigmentors, dermatitis herpetiformis suppressants, digestive aids, diuretics, dopamine receptor agonists, dopamine receptor antagonists, ectoparasiticides, emetics, enkephalinase inhibitors, enzymes, enzyme cofactors, estrogens, expectorants, fibrinogen receptor antagonists, fluoride supplements, gastric and pancreatic secretion stimulants, gastric cytoprotectants, gastric proton pump inhibitors, gastric secretion inhibitors, gastroprokinetics, glucocorticoids, α-glucosidase inhibitors, gonad-stimulating principles, growth hormone inhibitors, growth hormone releasing factors, growth stimulants, hematinics, hematopoietics, hemolytics, hemostatics, heparin antagonists, hepatic enzyme inducers, hepatoprotectants, histamine H2 receptor antagonists, HIV protease inhibitors, HMG CoA reductase inhibitors, immunomodulators, immunosuppressants, insulin sensitizers, ion exchange resins, keratolytics, lactation stimulating hormones, laxatives/cathartics, leukotriene antagonists, LH-RH agonists, lipotropics, 5-lipoxygenase inhibitors, lupus erythematosus suppressants, matrix metalloproteinase inhibitors, mineralocorticoids, miotics, monoamine oxidase inhibitors, mucolytics, muscle relaxants, mydriatics, narcotic antagonists, neuroprotectives, nootropics, NSAIDS, ovarian hormones, oxytocics, pepsin inhibitors, pigmentation agents, plasma volume expanders, potassium channel activators/openers, progestogens, prolactin inhibitors, prostaglandins, protease inhibitors, radio-pharmaceuticals, 5α-reductase inhibitors, respiratory stimulants, reverse transcriptase inhibitors, sedatives/hypnotics, serenics, serotonin noradrenaline reuptake inhibitors, serotonin receptor agonists, serotonin receptor antagonists, serotonin uptake inhibitors, somatostatin analogs, thrombolytics, thromboxane $A_2$ receptor antagonists, thyroid hormones, thyrotropic hormones, tocolytics, topoisomerase I and II inhibitors, uricosurics, vasomodulators including vasodilators and vasoconstrictors, vasoprotectants, xanthine oxidase inhibitors, and combinations thereof.

Further examples of suitable drug substances include, but are not limited to, acetohexamide, acetylsalicylic acid, alclofenac, allopurinol, atropine, benzthiazide, carprofen, carvedilol, celecoxib, chlordiazepoxide, chlorpromazine, clonidine, clozapine, codeine, codeine phosphate, codeine sulfate, deracoxib, diacerein, diclofenac, diltiazem, docetaxel, estradiol, etodolac, etoposide, etoricoxib, fenbufen, fenclofenac, fenprofen, fentiazac, flurbiprofen, griseofulvin, haloperidol, ibuprofen, indomethacin, indoprofen, ketoprofen, lorazepam, medroxyprogesterone acetate, megestrol, meloxicam, methoxsalen, methylprednisone, morphine, morphine sulfate, naproxen, nicergoline, nifedipine, niflumic, olanzapine, oxaprozin, oxazepam, oxyphenbutazone, paclitaxel, palperidone, phenindione, phenobarbital, piroxicam, pirprofen, prednisolone, prednisone, procaine, progesterone, pyrimethamine, risperidone, rofecoxib, asenapine, sulfadiazine, sulfamerazine, sulfisoxazole, sulindac, suprofen, tacrolimus, temazepam, tiaprofenic acid, tilomisole, tolmetic, valdecoxib, vorinostat, and ziprasidone.

Yet further exemplary drug substances include, but are not limited to, acenocoumarol, acetyldigitoxin, anethole, anileridine, benzocaine, benzonatate, betamethasone, betamethasone acetate, betamethasone valerate, bisacodyl, bromodiphenhydramine, butamben, chlorambucil, chloramphenicol, chlordiazepoxide, chlorobutanol, chlorocresol, chlorpromazine, clindamycin palmitate, clioquinol, clopidogrel, cortisone acetate, cyclizine hydrochloride, cyproheptadine hydrochloride, demeclocycline, diazepam, dibucaine, digitoxin, dihydroergotamine mesylate, dimethisterone, disulfuram, docusate calcium, dihydrogesterone, enalaprilat, ergotamine tartrate, erythromycin, erythromycin estolate, fenofibrate, flumethasone pivalate, fluocinolone acetonide, fluorometholone, fluphenazine enanthate, flurandrenolide, guaifenesin, halazone, hydrocortisone, itraconazole, levothyroxine sodium, methyclothiazide, miconazole, miconazole nitrate, nitrofurazone, nitromersol, oxazepam, pentazocine, pentobarbital, primidone, quinine sulfate, stanozolol, sulconazole nitrate, sulfadimethoxine, sulfaethidole, sulfamethizole, sulfamethoxazole, sulfapyridine, tacrolimus, testosterone, triazolam, trichlormethiazide, and trioxsalen.

The amount of drug substance in the free-flowing powder formulation of the invention ranges in an amount from about 0.01% to about 50% by weight of the total dry weight of the free-flowing powder formulation, for example between 1% and 15%. In certain embodiments, the amount of drug substance is 0.1%, 0.5%. 0.75%, 1%, 1.25%, 1.5%, 1.75%, 2%, 3%, 5%, 10%, 15%, 20%, 25%, 30%, 35%, 40%, 45%, and 50% by weight of the total composition. The amount of drug substance in the composition may also be expressed as a range between any of the above-listed individual percentages.

The process also tolerates a range of ratios of poorly water-soluble drug substance to lipid. In general, it is understood herein that the ratios of poorly water-soluble drug substances to lipid are such that a clear, homogenous solution is formed when the lipid, poorly water-soluble drug substance, surfactant, water partially miscible or water non-miscible solvent, solubilizing aid, and water components of the process are mixed together. For example, the ratios of poorly water-soluble drug substance to lipid may range from 1:0.1 to 1:100 (w/w). In various embodiments, the ratio of poorly water-soluble drug substance to phospholipid is about 0.1:1, or about 0.2:1, or about 0.3:1, or about 0.4:1, or about 0.5:1, or about 0.6:1, or about 0.7:1, or about 0.8:1, or about 0.9:1, or about 1:1, or about 1:0.9, or about 1:0.8, or about 1:0.7, or about 1:0.6, or about 1:0.5, or about 1:0.4, or about 1:0.3, or about 1:0.2, or about 1:0.1.

Surfactants

As discussed above, the free-flowing powder formulation of the invention also comprises a surfactant or combination of surfactants. Generally, as used herein, a surfactant is understood to be any pharmaceutically acceptable surfactant or combination of surfactants that is tolerated by the process. Examples of suitable pharmaceutically acceptable surfactants include, but are not limited to: D-α-tocopheryl polyethylene glycol 1000 succinate (Vitamin E-TPGS); polyoxylglycerides (e.g., polyethylene glycol fatty acid esters, stearoyl macrogolglycerides, glyceryl behenate, glyceryl palmitostearate (e.g. Vitamin E TPGS (tocopherol glyceryl succinate), pegylated glycerides, including those sold by Gattefossé (Saint-Priest, France) under the trade names Gelucire®, Labrafils, Labrasol, Compritol® 888 ATO RTM, and Precirol® ATO 5 RTM); poloxamers (e.g., block copolymer surfactants, such as poloxamer 188, poloxamer 235, poloxamer 404, and poloxamer 407, and those sold by BASF Chemical Co. under the trade names Pluronic® F87, Pluronic® F127, Pluronic® F68, Pluronic® L44, Pluronic® P123, and Pluronic® P85; poloxamine, Span® 80 (Sigma-Aldrich Co.), Myrj® (Croda Inc.), Brij® 35, and Brij® 58 (Pierce Protein Research Products), sodium lauryl sulfate (SLS), cetyl trimethylammonium bromide (CTAB), and polyoxyethylene sorbitan fatty acid esters sold under the trade names Tween® 20, Tween® 40, and Tween® 80 (Spectrum Chemicals & Laboratory Products, Gardena, Calif.), or combinations thereof.

The amount of surfactant the process of the invention adds generally such that the w/w ratio of surfactant to lipid that the process adds ranges from 1:0.1 to 1:50. For example, the ratio may be from 1:2 to 1:5. In various embodiments, the ratio of surfactant to phospholipid is about 0.1:1, or about 0.2:1, or about 0.3:1, or about 0.4:1, or about 0.5:1, or about 0.6:1, or about 0.7:1, or about 0.8:1, or about 0.9:1, or about 1:1, or about 1:0.9, or about 1:0.8, or about 1:0.7, or about 1:0.6, or about 1:0.5, or about 1:0.4, or about 1:0.3, or about 1:0.2, or about 1:0.1.

Partially Water-Miscible Solvents or Non-Water-Miscible Solvents

Herein, the term "miscible" refers to the ability of one or more components, such as liquids, solids and gases, to mix together to form a single, homogeneous phase. Thus, a solvent and a lipid are miscible if they can be mixed to form a single, homogenous liquid whose distinct components are recognized only at the molecular level. When solvents are "partially water-miscible," it means that the solvent can be mixed with water to form a single homogenous phase in a certain concentration range, but not at other concentration ranges. In keeping with the definition of "partially water-miscible," "non-water-miscible" solvents do not form a single, homogenous liquid when they are mixed with water.

The partially water-miscible solvent or non-water-miscible solvent component of the formulation of the invention includes any partially water-miscible solvent or non-water-miscible solvent that dissolves the poorly water-soluble active agent, surfactant, and phospholipid components of the formulation, and is tolerated by the process. Examples of suitable partially water-miscible solvent or non-water-miscible solvents include, but are not limited to, benzyl alcohol, chloroform, cyclohexane, dichloromethane, ethyl acetate, ethyl methyl ketone, diethyl ether, heptanes (e.g., 3-ethylpentane, heptane, 2-methylhexane, 3-methylhexane, 2,2-Dimethylpentane, 2,3-dimethylpentane, 2,4-dimethylpentane, 3,3-dimethylpentane, methylcyclohexane, and triptane), hexene, isopropanol, methoxypropyl acetate, and toluene, or combinations thereof.

The process of the invention adds an amount of water non-miscible or partially-miscible solvent that dissolves completely the poorly water-soluble drug substance, lipid, and surfactant components of the formulation of the invention, and additionally mixes the resulting solution with the water-miscible solvent, water, and solubilizing aid components of the inventive formulation to form a clear, homogenous solution. In various embodiments of the process, the amount of water non-miscible or partially miscible solvent is from about 1% to about 50% (vol/vol) of the total liquid content of the homogenous solution made by the process of the invention as calculated prior to the solvent removal step of the process. In certain embodiments, the amount of partially water-miscible solvent or non-water-miscible solvent comprises about 5% to 30%, 10% to 25%, or 15% to 20% of the total liquid content (vol/vol) of the homogenous solution made by the process as measured prior to the solvent removal step of the process step of process. Upon mixing the poorly water-soluble active ingredient, surfactant, and phospholipid components with the partially water-miscible solvent or non-water-miscible solvent, dissolution of the foregoing ingredients is may be accomplished by any appropriate technique known in the art. For example, dissolution may be accomplished by simple mixing or by stirring, at or above ambient temperature.

Solubilizing Aids

Many poorly soluble drugs will not dissolve into a partially water-miscible solvent or non-water-miscible solvent if they are not sufficiently soluble. Accordingly, the process of the invention adds a solubilizing aid to improve the dissolution of the poorly water-soluble drug substance added by the process. However, solubilizing aids are typically soluble only in aqueous. Therefore, the process dissolves a solubilizing aid or combination of solubilizing aids in water, and then adds a water-miscible solvent or combination of water-miscible solvents to the solubilizing aid solution. The process then adds the combined solution of solubilizing aid solution and water-miscible solvent to the solution of lipid, poorly water-soluble active ingredient, and surfactant made by the process to form a clear, homogenous solution in which no solutes precipitate.

With respect to the water added by the process of the invention to dissolve the solubilizing aid, the process adds an amount of water that dissolves completely the solubilizing aid, mixes the solubilizing aid and water solution with water-miscible solvent to form a solution that is then mixed with the water non-miscible or partially-miscible solvent containing dissolved poorly water-soluble drug substance, lipid, and surfactant to form a clear, homogenous solution. In various embodiments, the amount of water added by the process can vary from about 5% to 50%, 10% to 45%, 15% to 40%, 20% to 35%, 25% to 35%, 25% to 30%, or 30% to 35% of the total liquid content (vol/vol) of the homogenous solution made by the process as measured prior to the solvent removal step of the process step of process.

In certain embodiments, one or more solubilizing aids are dissolved completely in a water-miscible solvent, such as, for example, ethanol. In such embodiments, the solubilizing aid-water-miscible solvent may then be mixed with water, or a solubilizing aid-water solution, and additionally mixed with the other components added by the process as discussed above. The amount of water-miscible solvent added by the process in embodiments where one or more solubilizing aids are first directly and completely dissolved in the water-miscible solvent is an amount that additionally mixes with a solubilizing aid-water solution, or water alone, and is additionally added in water miscible solvent to form a solution that is then mixed with the water non-miscible or partially-miscible solvent containing dissolved poorly water-soluble drug substance, lipid, and surfactant to form a clear, homogenous solution.

The solubilizing aid component of the formulation made by the process may represent about 1% to 90% of the total weight of the solid content of the formulation. For example, in various embodiments of the formulation of the invention, the solubilizing component may be about 40%, 50%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, or 90% of the total weight of the solid content of the formulation.

The process and formulations of the invention tolerate any solubilizing aid or combination of solubilizing aids that is pharmaceutically acceptable. Examples of suitable solubilizing aids include, but are not limited to, Eudragit® E 100, Eudragit® E PO, or Eudragit® E 12,5 (Röhm GmbH & Co. KG), lactose, polydextrose and cyclodextrins (e.g., α-cyclodextrin, β-cyclodextrin or hydroxypropyl β-cyclodextrin, or derivatives of cyclodextrins), or any combination thereof. In certain embodiments, specific characteristics of the drug substance to be formulated by the process, such as, but not limited to, its solubility profile, or its chemical structure, may guide the determination of the appropriate solubilizing aid or combination of solubilizing aids to be used in the process.

Water-Miscible Solvents

The process of the invention adds an amount of water-miscible solvent that mixes with the water-solubilizing aid solution, and additionally mixes with the solvent solution component of the process described above that comprises non-miscible or partially-miscible solvent, poorly water-soluble drug substance, lipid, and surfactant to form a clear, homogenous solution. In various embodiments of the process, the amount of water-miscible solvent is from about 1% to about 90% (vol/vol) of the total liquid content of the homogenous solution made by the process as measured prior to the solvent removal step of the process. For example, in some embodiments the amount of water-miscible solvent may be about 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, 70%, 75%, 80%, 85%, or 90% of the total liquid content (vol/vol) of the homogenous solution made by the process as measured prior to the solvent removal step of the process.

Solvent Removal and Production of a Free-Flowing Powder

As discussed above, the process removes the solvent components from the final, clear homogeneous solution made by the process to yield a free-flowing powder. The process of the invention can perform this solvent removal step by any appropriate method known in the art. Examples of suitable methods to achieve solvent removal include, but are not limited to spray drying or coating the mixture onto a surface of a substrate.

In various embodiments of the process produces the free-flowing powder formulation by spray drying. Advantageously, spray drying mixtures to produce a powder allows for processing at lower temperatures than allowed by other common methods for making a powdered pharmaceutical formulation. Exemplary spray-drying processes and spray-drying equipment are described in K. Masters, Spray Drying Handbook (Halstead Press, New York, 4th ed., 1985), which is incorporated in its entirety herein. Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This helps to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

As stated above, an alternative method of removing solvent is to coat (typically by spray drying) the formulation made by the process on a surface of a substrate. In general, a substrate may be any water-soluble, inert material which is suitable for oral or parenteral use, but is poorly soluble or insoluble in the water partially miscible or water non-miscible solvent used by the process to dissolve the lipid, poorly water-soluble drug substance, and surfactant components of the inventive formulation. Suitable materials for such inert substrate materials include, but are not limited to sodium chloride, lactose, dextrose, and sucrose. For example, exemplary substrates include sugar beads In various embodiments, the clear, homogeneous solution made by the process of the invention can be applied to nonpareil beads. The nonpareil beads can be any inert bead, e.g., starch or sugar spheres such as nonpareil sugar beads that can be sieved through a mesh having any mesh size from number 10 to number 400, which correlates to a bead diameter size range of from about 37 to 2000 microns. For example, the mesh size number may be selected from, but is not limited to 20, 30, 40, 50, 60, 70, 80, 100, 120, 140, 170, and 200.

The clear, homogeneous solution made by the process of the invention can be applied to an inert substrate using any known technique. For example, the solution can be applied to nonpareil beads using a rotogranulator with tangential coating or a conventional coating pan with powder spraying/layering. Indeed, coating of a substrate generally involves the application of the homogenous solution in a rotating coating pan or in a fluidized bed. The surface of the substrate or the substrate itself may be heated to increase the rate of solvent removal.

Additional Modifications to the Formulation of the Invention

The process of the invention allows for further modification of the free-flowing powder formulation, or inert substrate coated by the formulation of the invention. For example, the process is flexible with regards to whether the final drug product is to be a capsule, tablet, or another dosage form is desired. Thus, the formulations of the invention may be further formulated into various dosage forms by methods known in the pharmaceutical formulation art, for example, see Remington's Pharmaceutical Sciences, 18th Ed., (Mack Publishing Company, Easton, Pa., 1990), which is incorporated herein by reference. For example, the free-flowing powdered formulation may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or combinations thereof. In the case of capsules, tablets, and pills, the dosage forms may also comprise buffering agents. Other formulations suitable for oral administration may be in the form of discrete units as capsules, sachets, or lozenges, in the form of a powder or granules; in the form of a solution or a suspension in an aqueous liquid or non-aqueous liquid, such as ethanol or glycerol; or in the form of an oil-in-water emulsion or a water-in-oil emulsion. A bolus, electuary or paste may also be relevant. Suitable oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms, such as pills or capsules as described above, may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or combinations of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Dispersed Particle Formation

Upon contact with an aqueous fluid, or an organic solvent, the free flowing powder of the invention instantaneously disperses into particles that contain the poorly water-soluble drug, phospholipid substance, and surfactant ingredients. For example, the free flowing powder formulation produced by the process instantaneously disperses into particles when it contacts aqueous environment typically found in the digestive tract, including saliva, physiological fluids, and ingested liquids. The particles may be spherical, and may vary in size. Generally, the particles have mean diameters of less than one millimeter; therefore, in various embodiments, the particles are nanoparticles. While the mean diameters of the nanoparticles may be from about 100 nm to about 500 nm, the diameters of the particles are generally from about 100 nm to 900 nm.

Once dispersed, the particles facilitate the increased in vivo dissolution and absorption of the poorly water-soluble drugs contained therein, as compared to poorly water-soluble drugs in pure form. More specifically, the particles increase the surface area of the poorly soluble active agent, thereby increasing the dissolution of the active agent, and the amount of the active agent that is released in a dosage form that becomes available for absorption in vivo. The particles of the invention can have desired drug release properties. In various embodiments, the particles that disperse from the inventive formulation in an aqueous environment, such as in bodily fluids, either release 60% or more, 80% or more, or 100% or more of the active agent that is contained in the particles within 10 minutes of contacting the aqueous solution. In other embodiments, the particles that disperse from the inventive formulation in an aqueous solution either release 60% or more, 80% or more, or 100% of the drug within 30 minutes.

EXAMPLES

Example 1

Method of Preparing a Free-Flowing Powder Formulation Comprising Phosphatidyl Choline and Itraconazole Egg phosphatidyl choline (200 mg), itraconazole (100 mg), and Gelucire® (50 mg) were dissolved in chloroform (5 ml) to form a solvent solution. Lactose (1000 mg) was dissolved in water (8 ml) to form a first aqueous solution. Methanol (14 ml) was slowly added to the first aqueous solution as the solution was being stirred in order to form a second aqueous solution. The solvent solution and the second aqueous solution were mixed to form a clear, homogenous solution, which was subsequently spray dried or coated onto sugar beads to yield a free flowing powder. Coating the homogenous solution on sugar beads was performed by loading 300-500 µm sugar beads onto a fluidized bed coater with top spray mechanism. The homogenous solution was spray coated at a rate of 0.1-0.5 ml/min while continuously fluidizing and heating the beads at 40-60° C. Coating levels of 5-30% w/w were achieved.

Following the formation of the free flowing powder, the powder was instantaneously dispersed into particles by adding 10 mg of powder to 5 ml of water. The suspension of particles was mildly shaken by hand. Dynamic light scattering analysis of particle diameter sizes was performed, and demonstrated that mean particle diameter size was 487 nm. In brief, the dynamic light scattering technique used to measure particle size and size distributions was performed using (NICOMP model 370 Submicron Particle Sizer, Santa Barbara, Calif.). Intensity-weighted Gaussian analysis was used for calculating unimodal distribution. The run time of the analysis stopped automatically when a fitting error of one or a Chi-squared value of less than 1 was achieved.

Example 2

Method of Preparing a Free-Flowing Powder Formulation Comprising Dimyristoyl-Phosphocholine and Itraconazole Dimyristoyl-phosphocholine (200 mg), itraconazole (100 mg), and Tween® 80 (100 mg) were dissolved in dichloromethane (5 ml) to form a solvent solution. Polydextrose (800 mg) was dissolved in water (9 ml) to form a first aqueous solution. Isopropyl alcohol (15 ml) was slowly added to the first aqueous solution as the solution was being stirred in order to form a second aqueous solution. The solvent solution and the second aqueous solution were mixed to form a clear, homogenous solution, which was subsequently spray dried to yield a free flowing powder. The free flowing powder was instantaneously dispersed into particles by adding 10 mg of dry powder to 5 ml of water. The suspension of particles was mildly shaken by hand. Dynamic light scattering analysis of particle diameter sizes was performed, and demonstrated that mean particle diameter size was 431 nm. Dynamic light scattering analysis was performed according as described in Example 1.

Example 3

Method of Preparing a Free-Flowing Powder Formulation Comprising Dimyristoyl-Phospho Glycerol and Itraconazole Dimyristoyl-phosphoglycerol (150 mg), itraconazole (100 mg), and Gelucire® surfactant (50 mg) were dissolved in dichloromethane (5 ml) to form a solvent solution. Lactose (400 mg) and hydroxy propyl β-cyclodextrin (200 mg) were dissolved in water (10 ml) to form a first aqueous solution. Ethanol (13 ml) was slowly added to the first aqueous solution as the solution was being stirred to form a second aqueous solution. The solvent solution and the second aqueous solution were mixed to form a clear, homogenous solution, which was subsequently spray dried to yield a free flowing powder. The free flowing powder was instantaneously dispersed into particles by adding 10 mg of powder to 5 ml of water. The suspension of particles was mildly shaken by hand. Dynamic light scattering analysis of particle diameter sizes was performed, and demonstrated that mean particle diameter size was 410 nm. Dynamic light scattering analysis was performed according as described in Example 1.

Example 4

In Vitro Release of Itraconazole from a Free-Flowing Powder Formulation Comprising Dimyristoyl-Phosphoglycerol and Itraconazole The dissolution profile of pure itraconazole was compared to the dissolution profile itraconazole from the free-flowing powder formulation that was made by the process described in Example 3. See FIG. 1. The amount of free flowing powder formulation used in the dissolution studies was equivalent to amount of the formulation containing 100 mg of itraconazole. The amount of pure itraconazole used as a control in the studies was also 100 mg. The free-flowing powder and pure itraconazole preparations were analyzed separately in 900 ml of simulated gastric fluid (pH 1.2) that did not contain enzymes. The analysis was performed using a USP Type II dissolution apparatus with the paddle speed and temperature maintained at 100 rpm and 37±0.5° C. Three ml aliquots were removed at 10, 20, 30, 45 and 60 minute intervals. Subsequently, the amount of itraconazole in each of the aliquots was determined by using an HP Agilent® 1100 series HPLC system (Agilent Technologies, Inc., Santa Clara, Calif.). The mobile phase solution used in the HPLC system consisted of 65% acetonitrile and 35% 10 mM potassium dihydrogen phosphate. The solution was pumped through a Phenomenex® Luna 5 μm C-18 (dimension: 150 mm×4.6 mm) column (Phenomenex Corp., Torrance Calif.) at a flow rate of 1.3 ml/min. Itraconazole was detected at a wavelength of 263 nm. Dynamic light scattering analysis was performed according as described in Example 1.

Example 5

Method of Preparing a Free-Flowing Powder Formulation Comprising Soy Phosphatidyl Choline and Itraconazole Soy Phosphatidyl Choline (190 mg), itraconazole (100 mg), and Poloxamer 188 (55 mg) were dissolved in dichloromethane (4 ml) to form a solvent solution. Eudragit® E (300 mg) was added to ethanol (7 ml). The Eudragit® E-ethanol solution was then added to the solvent solution. Lactose (400 mg) was dissolved in water (7 ml) to form a first aqueous solution. Ethanol (8 ml) was slowly added to the first aqueous solution as the solution was being stirred in order to form a second aqueous solution. The solvent solution and the second aqueous solution were mixed to form a clear, homogenous solution, which was subsequently spray dried or coated onto sugar beads to yield a free flowing powder. The step of coating the homogenous solution onto sugar beads was performed as described in Example 1.

The free flowing powder was instantaneously dispersed into particles by adding 10 mg of powder to 5 ml of water. The suspension of particles was mildly shaken by hand. Dynamic light scattering analysis of particle diameter sizes was performed, and demonstrated that mean particle diameter size was 319 nm. Dynamic light scattering analysis was performed according as described in Example 1.

Example 6

Figure 2:
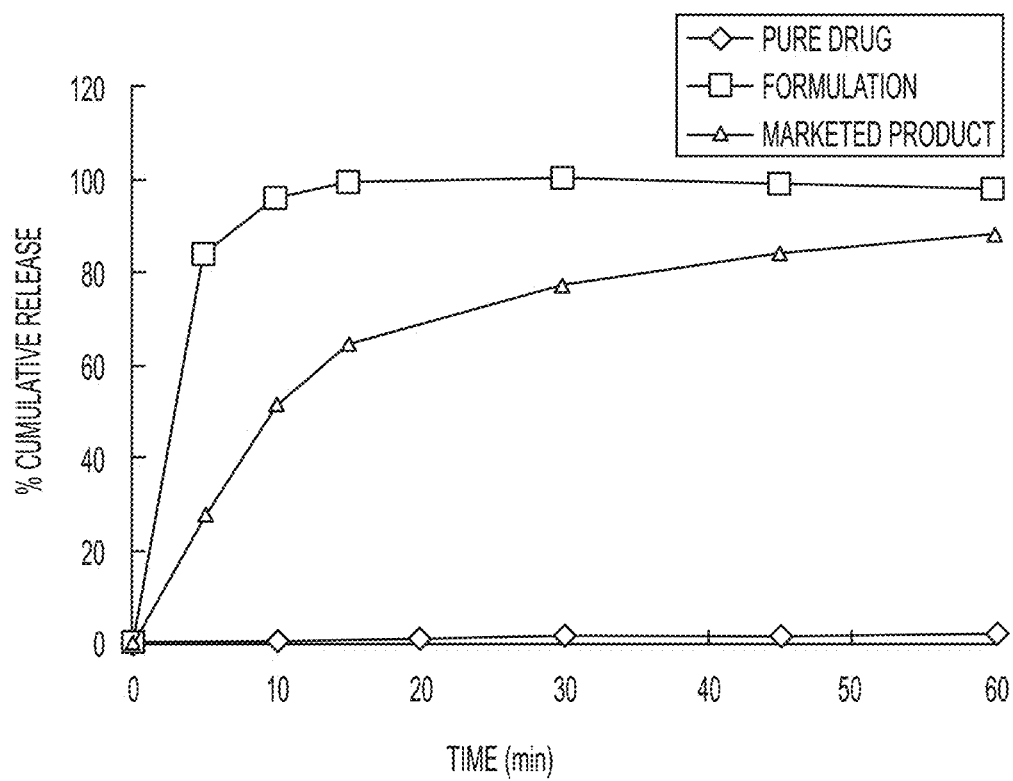
FIG. 2 shows the dissolution profile of itraconazole from a free-flowing powder itraconazole formulation comprising soy phosphatidyl choline as compared to the dissolution profiles of an equivalent amount of pure itraconazole, and a commercially marketed itraconazole formulation (Itraconazole Capsules, 100 mg, Sandoz, Princeton, N.J.).

In-Vitro Release of Itraconazole from a Free-Flowing Powder Formulation Comprising Soy Phosphatidyl Choline and Itraconazole The dissolution profile of pure itraconazole was compared to: the dissolution profile of a commercially marketed itracanazole formulation (Itraconazole Capsules, 100 mg, manufactured by Sandoz, Princeton, N.J.); and to the dissolution profile itraconazole from the free-flowing powder formulation that was made by the process described in Example 5. See FIG. 2. The amount of free flowing powder formulation used in the dissolution studies was equivalent to amount of the formulation containing 100 mg of itraconazole. The amounts of pure itraconazole and marketed itraconazole used as controls also consisted of 100 mg doses. The free-flowing, pure, and marketed formulations of itraconazole were analyzed separately in 900 ml of simulated gastric fluid (pH 1.2) that did not contain enzymes. The analysis was performed using a USP Type II dissolution apparatus with the paddle speed and temperature maintained at 100 rpm and 37±0.5° C. Three ml aliquots were removed at 10, 20, 30, 45 and 60 minute intervals. Subsequently, the amount of itraconazole in each of the aliquots was determined by using an HP Agilent® 1100 series HPLC system (Agilent Technologies, Inc., Santa Clara, Calif.). The mobile phase solution used in the HPLC system consisted of 65% acetonitrile and 35% 10 mM potassium dihydrogen phosphate. The solution was pumped through a Phenomenex® Luna 5 μm C-18 (dimension: 150 mm×4.6 mm) column (Phenomenex Corp., Torrance Calif.) at a flow rate of 1.3 ml/min. Itraconazole was detected at a wavelength of 263 nm. Dynamic light scattering analysis was performed according as described in Example 1.

Example 7

Comparison of the In-Vitro Release of Itraconazole from Free-Flowing Powder Formulation Comprising Soy Phosphatidyl Choline and Either Lactose, Polydextrose, or Hydroxyl β-Cyclodextrin The effects of various solubilizing aids on the dissolution profile of itraconazole from free flowing powder formulations comprising itraconazole and soy phosphatidyl choline were determined by assessing the dissolution profiles from three separate formulation preparations that were made using either lactose, polydextrose, or hydroxyl β-cyclodextrin, respectively. Each of the three formulations were made according to the method described by Example 5, with the exception that that the respective formulations contained either lactose, polydextrose, or hydroxyl β-cyclodextrin as the solubilizing aid components. More specifically, the solubilizing aid component of the formulations was either 400 mg of lactose in 7 ml of water, 800 mg of polydextrose to 7 ml of water, or 200 mg of hydroxyl β-cyclodextrin in 7 ml of water.

The free-flowing powders were instantaneously dispersed into particles by respectively adding 10 mg of free-flowing powder formulation to 5 ml of water. The suspensions of particles were each mildly shaken by hand. Dynamic light scattering analysis of the dispersed particles' diameter sizes were performed. Dynamic light scattering analysis was performed according as described in Example 1. The dispersed particles were spherical in shape as observed under an optical microscope and mean particle sizes were in the range of 200 to 900 nm. The particles that dispersed from the free-flowing powder using lactose as a solubilizing aid had lowest mean particle size of 282 nm. The formation of dispersed particles was confirmed by observing the process of hydration of spray dried formulations under an optical microscope at 400× magnification.

Figure 3:
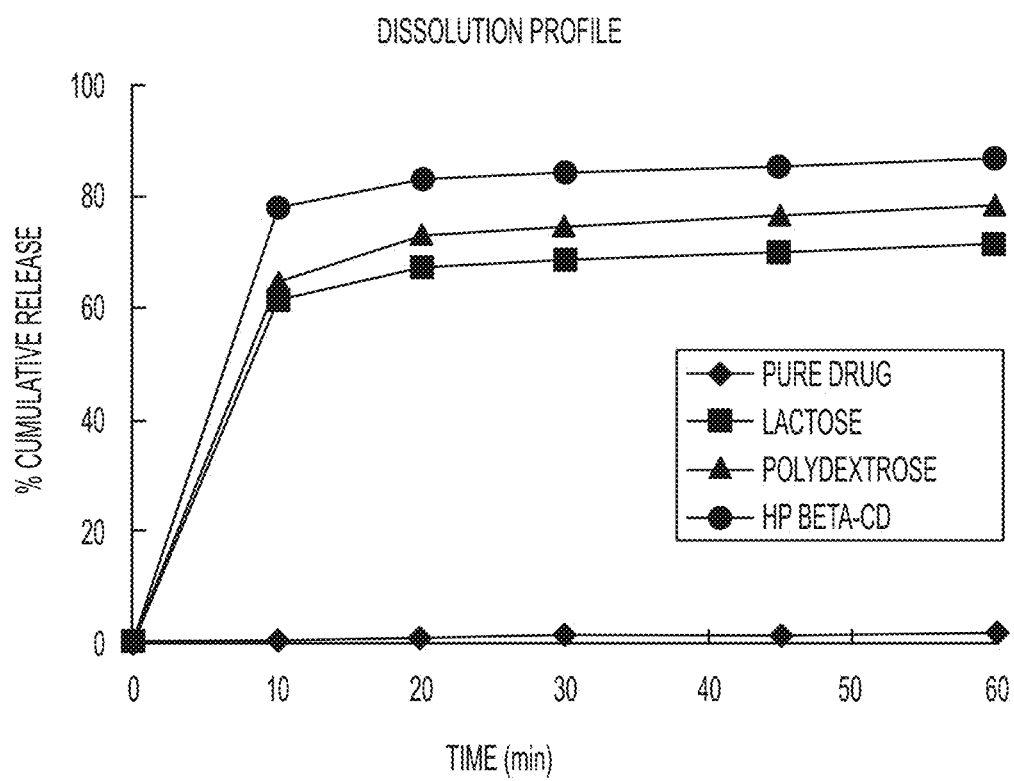
FIG. 3 compares the dissolution profiles of pure itraconazole to free-flowing powder itraconazole formulations comprising either lactose, polydextrose, or hydroxypropyl β-cyclodextrin as solubilizing aids, respectively.

In vitro dissolution release profiles for itraconazole were obtained for the free-flowing powder formulations comprising either lactose, polydextrose, or hydroxyl β-cyclodextrin, respectively, according to the methods used in examples 4, 6, and 7. Pure itraconazole (100 mg) was used as a control. Regardless of whether lactose, polydextrose, or hydroxyl β-cyclodextrin was used as a solubilizing aid, significant increase in dissolution of drug was observed. The dissolution profiles of pure drug and different free-flowing powder formulations are presented in FIG. 3. Each free-flowing powder formulation released more than 60% of drug in just 10 min, whereas less than 1% drug release occurred in 10 min with pure drug.

Example 8

Method of Preparing a Free-Flowing Powder Formulation Comprising Soy Phosphatidyl Choline and Fenofibrate Soy Phosphatidyl Choline (200 mg), fenofibrate (100 mg), and Vitamin E TPGS (60 mg) were dissolved in dichloromethane (5 ml) to form a solvent solution. Lactose (500 mg) and hydroxy propyl β-cyclodextrin (80 mg) were dissolved in water (9 ml) to form a first aqueous solution. Ethanol was slowly added to the first aqueous solution as the solution was being stirred in order to form a second aqueous solution. The solvent solution and the second aqueous solution were mixed to form a clear, homogenous solution, which was subsequently spray dried or coated onto sugar beads to yield a free flowing powder. The step of coating the homogenous solution onto sugar beads was performed as described in Example 1.

The free flowing powder was instantaneously dispersed into particles by adding 10 mg of powder to 5 ml of water. The suspension of particles was mildly shaken by hand. Dynamic light scattering analysis of particle diameter sizes was performed, and demonstrated that mean particle diameter size was 151 nm. Dynamic light scattering analysis was performed according as described in Example 1.

Example 9

Figure 4:
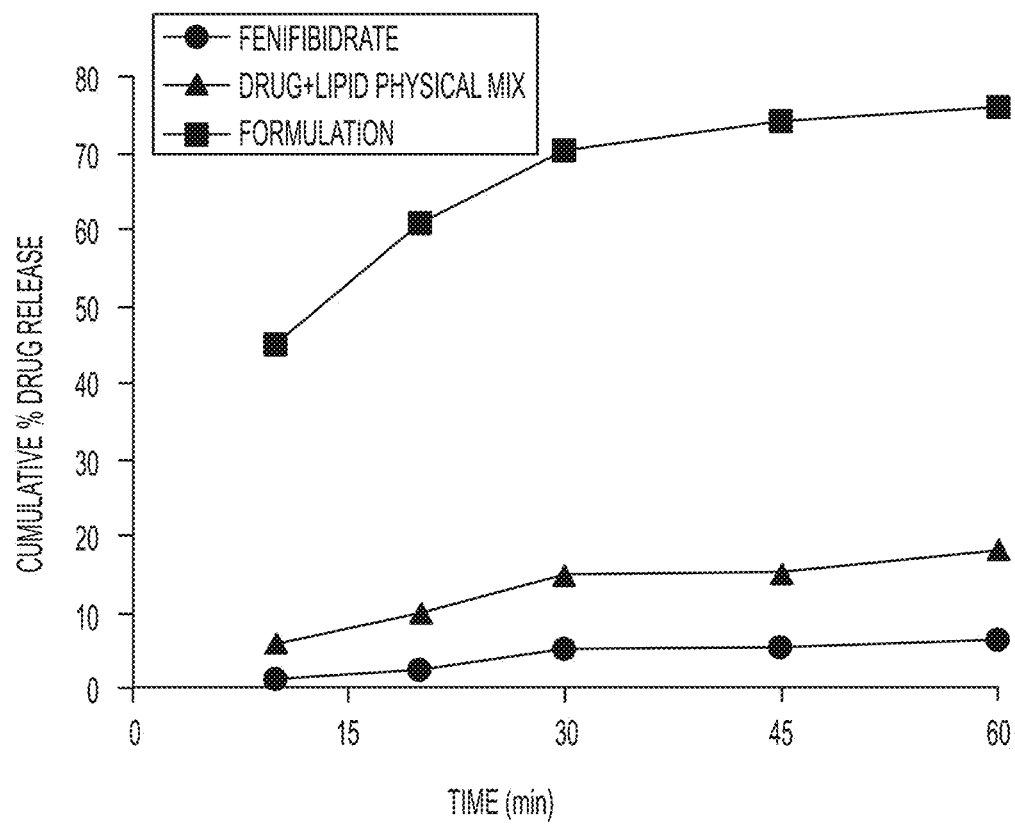
FIG. 4 compares the dissolution profiles of pure fenofibrate, a commercially marketed fenofibrate formulation (Tricor® 145 mg tablets, manufactured by Abbott Laboratories. Abbott Park, Ill., U.S.A), and a free flowing powder fenofibrate formulation.

In-Vitro Release of Fenofibrate from Particles Dispersed from a Free-Flowing Powder Formulation Using Soy Phosphatidyl Choline and Fenofibrate The dissolution profile of pure fenofibrate was compared to: the dissolution profile of a commercially marketed fenofibrate formulation (Tricor® 145 mg tablets, manufactured by Abbott Laboratories. Abbott Park, Ill., U.S.A); and to the dissolution profile of fenofibrate from the free-flowing powder formulation that was made by the process described in Example 8. See FIG. 4. The amount of free flowing powder formulation used in the dissolution studies was equivalent to the amount of the formulation containing 145 mg of fenofibrate. The amounts of pure fenofibrate and Tricor® 145 used as controls also consisted of 145 mg doses. The free-flowing powder, pure, and Tricor® 145 formulations were analyzed separately in 900 ml of simulated gastric fluid, which had a pH 1.2, and did not contain enzymes. The analysis was performed using a USP Type II dissolution apparatus with the paddle speed and temperature maintained at 100 rpm and 37±0.5° C. Three ml aliquots were removed at 10, 20, 30, 45 and 60 minute intervals. Subsequently, the amount of itraconazole in each of the aliquots was determined by using an HP Agilent® 1100 series HPLC system (Agilent Technologies, Inc., Santa Clara, Calif.). The mobile phase solution used in the HPLC system consisted of 65% acetonitrile and 35% 10 mM potassium dihydrogen phosphate. The solution was pumped through a Phenomenex® Luna 5 μm C-18 (dimension: 150 mm×4.6 mm) column (Phenomenex Corp., Torrance Calif.) at a flow rate of 1.3 ml/min. Dynamic light scattering analysis was performed according as described in Example 1.

Example 10

TEM of Particles Dispersed from a Fenofibrate Powder Formulation

Figure 5:
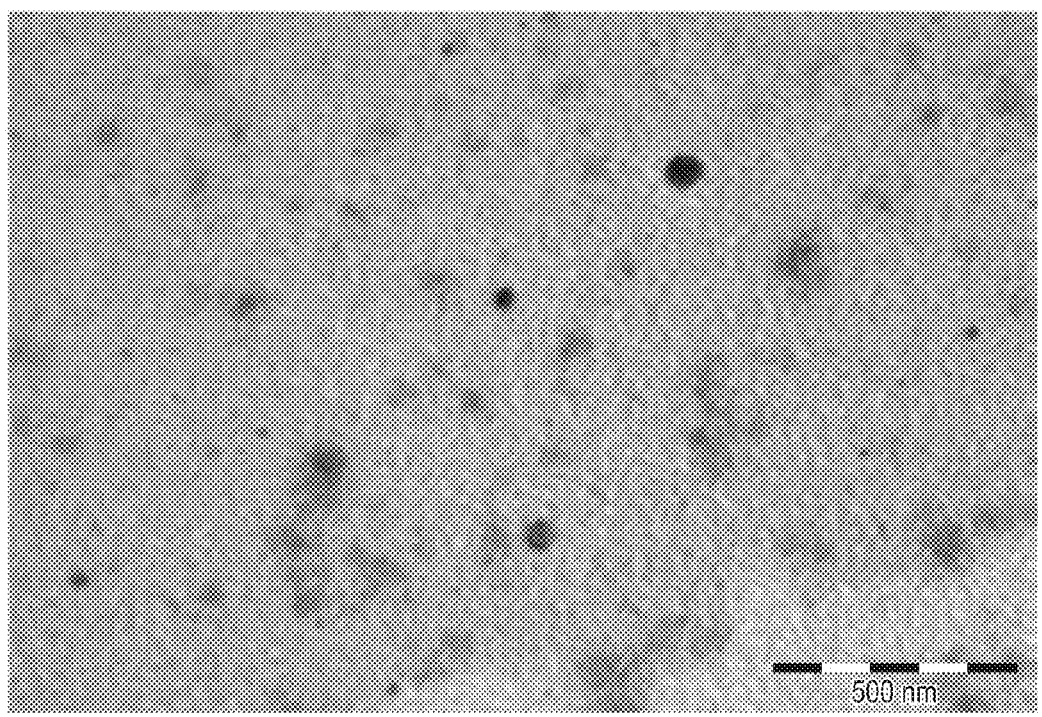
FIG. 5 shows a transmission electron micrograph of particles dispersed in an aqueous solution from a free-flowing powder fenofibrate formulation. Scale bar=500 nm.

The morphology of particles dispersed from a fenofibrate powder formulation made according to the method in Example 7 was observed under a FEI Tecnai G2 Spirit transmission electron microscope (Eindhoven, Netherlands). The particles were formed by adding 10 mg of powder to 5 ml of water followed by mild hand shaking of the suspension. The free flowing powder instantaneously dispersed into particles under these conditions. A drop of the suspension of the disperded particles was dried on a carbon-coated grid and stained with aqueous solution of phosphotungstic acid. After drying the specimen was viewed under the microscope at an accelerating voltage of 100 kV Transmission electron micrographs (TEM) confirmed the presence of particles that dispersed from the free flowing powder fenofibrate formulation. A TEM image of the dispersed particles is shown in FIG. 5.

Example 11

DSC Analyses

Differential scanning calorimetry (DSC) was performed to understand the physical state of fenofibrate in a free-flowing powder formulation comprising fenofibrate and soy phosphatidyl choline prepared as described in Example 8.

Figure 6:
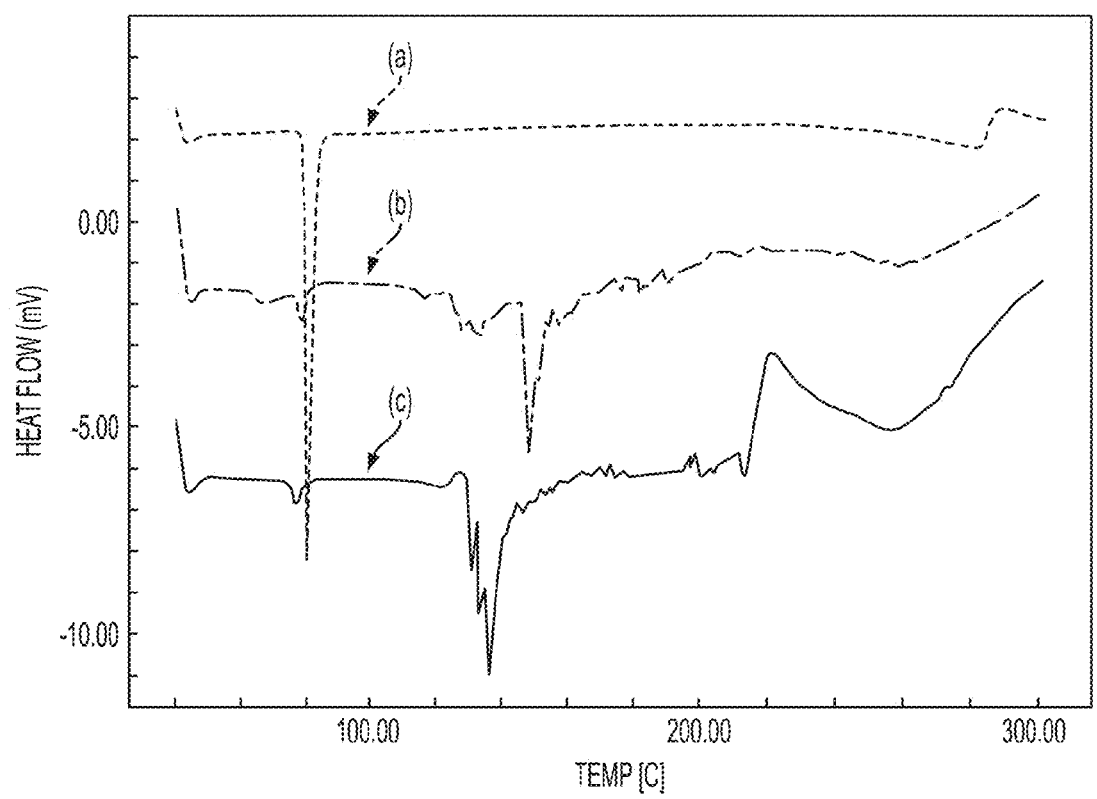
FIG. 6 compares DSC thermograms of pure fenofibrate, a physical mixture of fenofibrate and phospholipid (soy phosphatidyl choline), and a free-flowing powder fenofibrate formulation.

DSC was performed on pure fenofibrate, a physical mixture of fenofibrate and phospholipid (soy phosphatidyl choline), as well as a free-flowing powder formulation compring fenofibrate. Samples were analyzed using Shimadzu DSC-60 (Kyoto, Japan) in nitrogen environment with a heating rate of 10° C./min. The DSC thermograms for pure drug, drug, and phospholipid (DMPC) physical mixture and free-flowing powder mixture are presented in FIG. 6. It is evident from the results that, in the physical mixture, ΔH has reduced drastically and the peak shifts to the lower temperature. In the physical mixture, phospholipid could be dominating the transitions and hence a broader peak is observed with lower ΔH value.

Example 12

Comparison of the In-Vitro Release of Fenofibrate from Free-Flowing Powder Formulations Comprising Either Dimyristoyl-Phosphoglycerol, Dimyristoyl-Phosphocholine, Egg Phosphatidylcholine, or Soy Phosphatidyl Choline The effect of various phospholipids on the dissolution profile of fenofibrate from free flowing powder formulations comprising fenofibrate and either dimyristoyl-phosphoglycerol, dimyristoyl-phosphocholine, egg phosphatidylcholine, or Soy Phosphatidyl Choline was determined. See FIG. 7. Separate formulations were made for each of the foregoing phospholipids according to the method described by Example 8.

The free-flowing powders were instantaneously dispersed into particles by respectively adding 10 mg of free-flowing powder formulation to 5 ml of water. The suspensions of particles were each mildly shaken by hand. Dynamic light scattering analysis of the dispersed particles' diameter sizes were performed. Dynamic light scattering analysis was performed according as described in Example 1. The formation of dispersed particles was confirmed by observing the process of hydration of spray dried formulations under an optical microscope at 400× magnification.

Figure 7:
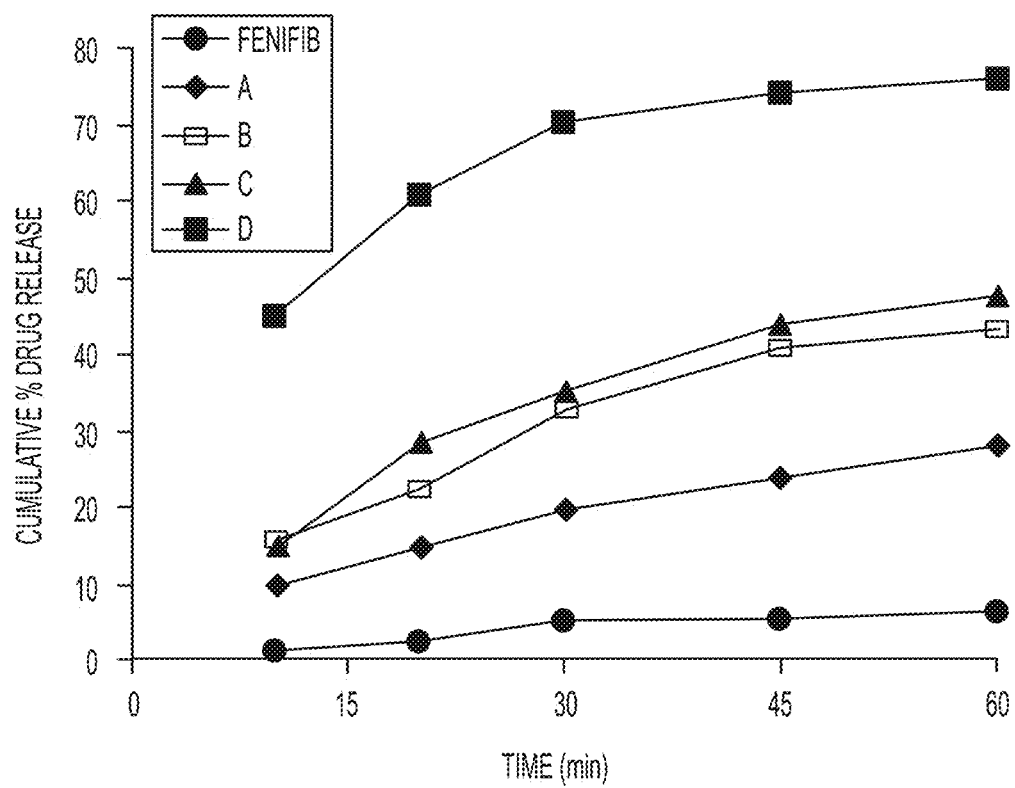
FIG. 7 compares the in-vitro release profiles of fenofibrate from free-flowing powder formulations comprising either dimyristoyl-phosphoglycerol (line A), dimyristoyl-phosphocholine (line B), egg phosphatidylcholine (line C), or soy phosphatidyl choline (line D).

The in vitro dissolution release profiles for the formulations comprising the different lipid ingredients are shown in FIG. 7, and were obtained for each of the foregoing free-flowing powder formulations according to the methods used in Example 9.

Example 13

In Vivo Pharmacokinetic Analysis Following the Administration of a Free-Flowing Powder Formulation of Fenofibrate The bioavailability of the poorly water-soluble drug, fenofibrate, was studied in rats following the oral administration of the free-flowing powder formulation described in Example 8, the commercially marketed fenofibrate drug, Tricor®, and pure fenofibrate. See FIG. 8. The study was performed on jugular vein-cannulated rats weighing from 200 to 250 gm (n=4). The inventive formulation, the Tricor® formulation, and pure fenofibrate were each suspended in an aqueous 0.5% sodium carboxymethyl cellulose solution prior to being administered to the respective rats. The inventive formulation and the Tricor® formulation formed suspensions, wherein the fenofibrate remained chemically stable, and solutes did not precipitate out of solution and form a hard cake on the bottom of a container upon storage.

Figure 8:
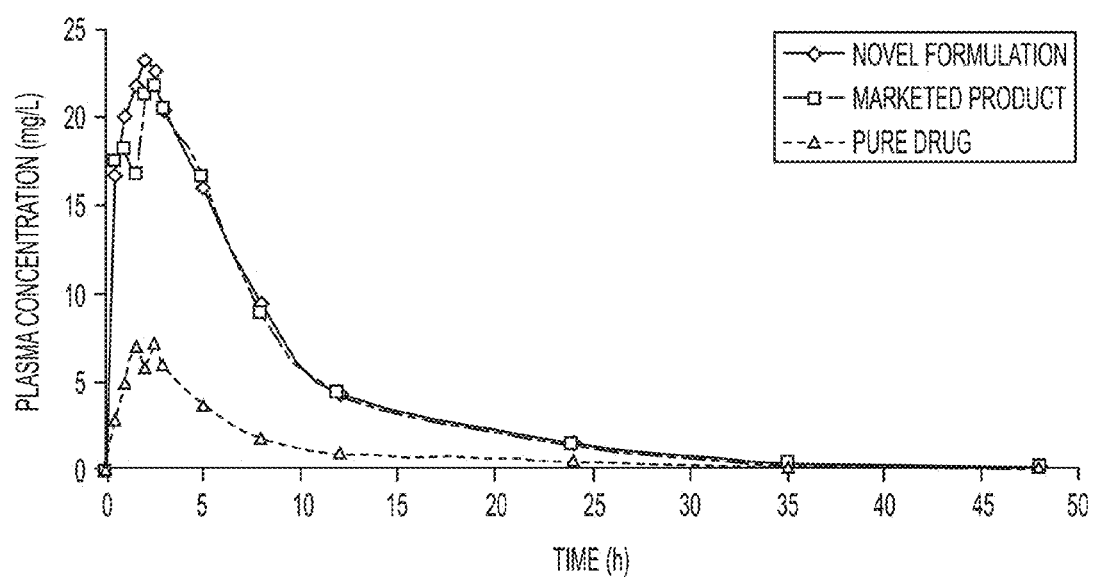
FIG. 8 In vivo pharmacokinetic analysis following the administration of a free-flowing powder formulation of fenofibrate, a physical mixture of fenofibrate and phospholipid, and pure fenofibrate.

Pure fenofibrate did not form a stable suspension; particles settled at the bottom of solution container. Each rat was orally administered a clinical dose of fenofibrate (145 mg/70 kg) in a volume of 1.5 ml. Blood samples were collected at various time intervals over a 48 hour period after administration. The samples were collected into heparinized tubes through the jugular vein cannulation, centrifuged at 5000 rpm for 5 minutes. Each 50 µl plasma sample was treated with 10 µl of 50% methanol and 10 µl of an internal standard (Indomethacin), and then mixed by vortexing for 30 seconds. To that mixture, 200 µl of acetonitrile was added, followed by one minute of vortexing, centrifugation at 14,000 rpm for five minutes. Plasma concentrations of the fenofibrate active metabolite, fenofibric acid, were determined by Liquid Chromatography-Mass Spec (LCMS). Indomethacin was used as an internal standard for the LCMS analyis. Standard non-compartmental pharmacokinetic parameters were calculated. Briefly, noncompartmental pharmacokinetic analysis is dependent on estimation of total drug exposure. Total drug exposure is most often estimated by area under the curve (AUC) using the trapezoidal rule (numerical integration) method. Due to the dependence on the length of 'x' in the trapezoidal rule, the area estimation is dependent on the blood/plasma sampling schedule. That is, the closer time points are, the closer the trapezoids reflect the actual shape of the concentration-time curve. FIG. 8 shows the blood/plasma fenofibrate concentrations over time following the administration of the free-flowing powder formulation described in Example 8, the Tricor® formulation, and pure fenofibrate, respectively.

The inventive formulation and Tricor® showed area under the curve (AUC) values over 48 hours of 209 mg·h/L and 205 mg·h/L, respectively. The $AUC_{0-48}$ value for pure fenofibrate was 51 mg·h/L. The inventive formulation exhibited a $C_{max}$ value of 23.2 mg/L, and a $T_{max}$ value of 2 h. Similarly, Tricor® exhibited a $C_{max}$ of 21.7 mg/L, and a $T_{max}$ value of 2.5 h. Pure fenofibrate exhibited a $C_{max}$ value of 7.2 mg/L, and a $T_{max}$ value of 2.5 h. The mean residence times (MRT) of the inventive formulation, the Tricor® formulation, and pure fenofibrate were 8.37 h, 8.63 h, and 9.15 h, respectively. There were no statistically significant differences (p<0.05) between the $AUC_{0-48}$ and MRT values between the inventive formulation and the Tricor® product. The foregoing in vivo pharmacokinetic data is also provided in Table 1, below.

TABLE 1

|  | Formulation | Tricor® | Pure Drug |
|---|---|---|---|
| $C_{max}$ (mg/L) | 23.2 | 21.7 | 7.2 |
| $t_{max}$ (h) | 2 | 2.5 | 2.5 |
| $AUC_{0-t}$ (mg · h/L) | 209 | 205 | 51 |
| MRT (h) | 8.37 | 8.63 | 9.15 |
| $t_{1/2}$ (h) | 6.42 | 6.58 | 7.18 |
| CL (L/h) | 0.02 | 0.02 | 0.07 |
| $AUMC_{0-t}$ (mg · h/L) | 1662.75 | 1674.26 | 436.7 |

The claimed invention is:
1. A free-flowing powder comprising a homogenous solid dispersion consisting of:
    (a) a phospholipid component selected from soy phosphatidyl choline, egg phosphatidyl choline, dimyristoyl-phosphocholine, dimyristoyl-phosphoglycerol, distearoyl-phosphatidylcholine, distearoyl-phosphatidylglycerol, Dipalmitoyl-phosphocholine, or a combination thereof;
    (b) a poorly water-soluble drug substance component;

(c) a surfactant component; and (d) a solubilizing aid component selected from lactose, polydextrose, a cyclodextrin, an amino alkyl methacrylate copolymer, or a combination thereof, and (a), (b), (c), and (d) are present in weight/weight ratios (a:b:c:d) of (1.5-2):1:(0.5-1):(5.8-10).

2. The free-flowing powder formulation of claim 1, wherein the poorly water-soluble drug substance component requires 100 to 1,000 parts of water to one part poorly water-soluble drug substance to achieve solubility.

3. The free-flowing powder formulation of claim 1, wherein the surfactant component is Vitamin E d-α-tocopheryl polyethylene glycol 1000 succinate (Vitamin E TPGS), a polyoxylglyceride, a poloxamer, poloxamine, a sorbitan oleate, a polyoxyethylene stearate, a nonionic polyoxyethylene, sodium lauryl sulfate (SLS), cetyl trimethylammonium bromide (CTAB), polysorbate 20, polysorbate 40, and polysorbate 80, or a combination thereof.

4. A dispersed particle formed by the dispersion into particles of the free flowing powder of claim 1 in an aqueous solvent or an organic solvent, wherein the bulk distribution of the drug substance of the free flowing powder in the dispersed particle is uniform, and wherein the particle ranges in size from about 150 to 850 nm in diameter.

5. The free-flowing powder of claim 1, wherein the poorly water-soluble drug substance component is itraconazole or fenofibrate.

6. A free-flowing powder according to 1, wherein the solubilizing aid component constitutes from 59% to 76% of the total combined weights of the phospholipid, poorly water-soluble drug substance, surfactant, and solubilizing aid components.

\* \* \* \* \*